(12) United States Patent
Tobinick

(10) Patent No.: US 6,471,961 B1
(45) Date of Patent: Oct. 29, 2002

(54) INTERLEUKIN ANTAGONISTS FOR THE TREATMENT OF NEUROLOGICAL, RETINAL AND MUSCULAR DISORDERS

(76) Inventor: Edward L. Tobinick, 100 OCLA Medical Plz., Los Angeles, CA (US) 90024-6903

( * ) Notice: Subject to any disclaimer, the term of this patent is extended or adjusted under 35 U.S.C. 154(b) by 0 days.

(21) Appl. No.: 09/563,651

(22) Filed: May 2, 2000

(51) Int. Cl.⁷ .............................................. A61K 31/495
(52) U.S. Cl. ..................... 424/134.1; 514/249; 514/323
(58) Field of Search ........................ 424/134.1; 514/249, 514/323

(56) References Cited

U.S. PATENT DOCUMENTS

| | | | | |
|---|---|---|---|---|
| 5,075,222 A | * | 12/1991 | Hannum et al. | 435/69.1 |
| 5,187,162 A | * | 2/1993 | Marangos et al. | 514/46 |
| 5,863,769 A | * | 1/1999 | Young | 435/69.52 |
| 6,013,253 A | * | 1/2000 | Martin et al. | 424/85.7 |
| 6,015,557 A | * | 1/2000 | Tobinick et al. | 424/134.1 |
| 6,177,077 B1 | * | 1/2001 | Tobinick | 424/134.1 |

* cited by examiner

*Primary Examiner*—James H. Reamer
(74) *Attorney, Agent, or Firm*—Ezra Sutton

(57) ABSTRACT

Interleukin (IL) antagonists are provided for the treatment in humans of neurological disorders, trauma, injuries or compression; neurodegenerative disorders including Alzheimer's Disease; demyelinating neurological disorders including multiple sclerosis; retinal disorders; and muscular disorders. The IL antagonists are used to treat these disorders by inhibiting the action of IL in the human body. The administration of these IL antagonists is performed by intrathecal administration; intracerebroventricular administration; intranasal administration; by inhalation; or by alternative routes of administration.

30 Claims, No Drawings

INTERLEUKIN ANTAGONISTS FOR THE TREATMENT OF NEUROLOGICAL, RETINAL AND MUSCULAR DISORDERS

FIELD OF THE INVENTION

The present invention relates to interleukin (IL) antagonists for the treatment of neurological disorders, trauma, injuries or compression; neurodegenerative disorders including Alzheimer's Disease; demyelinating neurological disorders including multiple sclerosis; retinal disorders; and muscular disorders. More particularly, the IL antagonists are used in a new treatment of these disorders by inhibiting the action of IL in the human body. The administration of these IL antagonists is performed by intrathecal administration; intracerebroventricular administration; intranasal administration; by inhalation; or by alternative routes of administration.

BACKGROUND OF THE INVENTION

Neurological disorders due to demyelinating disease (e.g. multiple sclerosis), immune disease, inflammation, trauma, or compression, occur in different clinical forms depending upon the anatomic site and the cause and natural history of the physiological problem. Common to all of these disorders is the fact that they can cause permanent neurological damage, that damage can occur rapidly and be irreversible, and that current treatment of these conditions is unsatisfactory, often requiring surgery and/or the use of pharmacologic agents, which are often not completely successful.

These neurological conditions include acute spinal cord trauma, spinal cord compression, spinal cord hematoma, cord contusion (these cases are usually traumatic, such as motorcycle accidents or sports injuries); nerve compression, the most common condition being a herniated disc causing sciatic nerve compression, neuropathy, and pain; but also including cervical disc herniation, causing nerve compression in the neck; acute or chronic spinal cord compression from cancer (this is usually due to metastases to the spine, such as from prostate, breast or lung cancer); autoimmune disease of the nervous system; and demyelinating diseases, the most common condition being multiple sclerosis. Tissues related to the neurological system, those being the retina, optic nerve, and muscle, can be similarly affected.

Steroid drugs, such as cortisone, that are used to treat the aforementioned neurological problems and conditions are particularly hazardous because they are used either at high dosage, with a corresponding increasing risk of side effects, or because they are used chronically, also increasing their adverse effects. Lastly, steroids are only partially effective or completely ineffective.

Members of the interleukin family, including interleukin 1(IL-1), have been demonstrated to be key components of inflammation of the central nervous system and the retina. Antagonists of these cytokines which are in development include interleukin 1 receptor antagonist (IL-1 RA) and interleukin 1 receptor type II (IL-1R type II). Other interleukin antagonists which are the subject of this patent include the following: monoclonal antibodies to interleukin 1 (including both chimeric and fully humanized forms); soluble receptors to interleukin 1; soluble receptors to interleukin 1 fused to an $F_c$. Immunoglobulin fragment (a fusion protein, similar to etanercept except substituting IL-1 for TNF). Use of these interleukin antagonists can suppress this inflammation, which is important to the pathogenesis of a variety of clinical disorders. These disorders include uveoretinitis and the neurodegenerative diseases, including Alzheimer's Disease and Parkinson's Disease.

Clinical development of the interleukin antagonists has been confined to use for arthritis. For this use, peripheral administration is effective. The blood-brain barrier, however, interferes with the penetration of peripherally administered interleukin antagonists. Therefore, the use of these agents by intravenous, subcutaneous, intramuscular, or other peripheral routes will be less effective for the treatment of disorders of the central nervous system (including the brain and spinal cord) or the retina.

The inventor has received U.S. Pat. No. 6,015,557 for the use of TNF antagonists for the treatment of neurological disorders. Included in this patent is the intrathecal use of TNF antagonists. The present patent introduces the novel concept of the intrathecal administration of interleukin antagonists. Intrathecal administration (administration directly into the cerebrospinal fluid), either at the level of the spinal cord, or directly into the cerebroventricular system, allows these antagonists to reach the brain, spinal cord, or retina in therapeutically effective amounts. Peripheral administration of these agents for these uses may be less effective. These uses will ameliorate inflammation, and will therapeutically improve a variety of disorders with inflammatory or autoimmune components.

Acute and/or chronic intrathecal therapy with interleukin antagonists is thereby presented as a treatment for a diverse variety of acute and chronic neurological, retinal and muscular disorders, including:

Alzheimer's Disease
Parkinson's Disease
Pick's Disease
Huntington's Disease
Neurodegenerative Diseases
AIDS Dementia Complex
Inflammatory Diseases of the Brain, Spinal Cord, or Retina
Autoimmune Diseases of the Brain, Spinal Cord, or Retina
Multiple Sclerosis
Spinal Cord Injury
Spinal Cord Compression
Herniated Disc
Traumatic Brain Injury
Muscular Dystrophy
Polymyositis—Dermatomyositis There remains a need for a new pharmacologic treatment of these aforementioned physiological problems of the nervous system, retina, and muscle, associated with inflammation, autoimmune disease, demyelinating diseases, trauma, injuries and compression. The pharmacological use of IL antagonists are greatly beneficial for the large number of patients whom these conditions affect. IL antagonists may be used for the immediate, short term and long term (acute and chronic) blockade of IL in order to minimize neurologic damage mediated by IL dependent processes occurring in the aforementioned neurological disorders. The use of these IL antagonists will result in the amelioration of these physiological neurological, retinal and muscular disorders. Intrathecal administration of the IL antagonists is the preferred treatment for disorders of the central nervous system, including Alzheimer's disease and other neurodegenerative diseases; and for disorders of the optic nerve and the retina.

DESCRIPTION OF THE PRIOR ART

Pharmacologic chemical substances, compounds and agents which are used for the treatment of neurological disorders, trauma, injuries and compression having various organic structures and metabolic functions have been disclosed in the prior art. For example, U.S. Pat. Nos. 5,756,482 and 5,574,022 to ROBERTS et al disclose methods of attenuating physical damage to the nervous system and to the spinal cord after injury using steroid hormones or steroid precursors such as pregnenolone, and pregnenolone sulfate in conjunction with a non-steroidal anti-inflammatory substance such as indomethacin. These prior art patents do not teach the use of IL-1 antagonists or IL-1 blocker for the suppression and inhibition of the action of IL-1 in the human body to treat neurological disease, trauma, injury or compression, or autoimmune neurologic disease as in the present invention.

U.S. Pat. No. 5,650,396 discloses a method of treating multiple sclerosis (MS) by blocking and inhibiting the action of TNF in a patient. This prior art patent does not teach the use of the IL-1 antagonists as in the present invention.

U.S. Pat. No. 5,863,769 discloses using IL-1 RA for treating various diseases. However, it does not disclose administering IL Blockers intrathecally into the cerebrospinal fluid (CSF), as in the present invention.

U.S. Pat. No. 6,013,253 discloses using interferon and IL-1 RA for treating multiple sclerosis. However, it does not disclose administering IL Blockers intrathecally into the cerebrospinal fluid (CSF) for treating Alzheimer's and related diseases.

U.S. Pat. No. 5,075,222 discloses the use of IL-1 inhibitors for treatment for various disorders. However, it does not disclose administering IL Blockers intrathecally into the CSF for treating Alzheimer's and related diseases.

None of the prior art patents disclose or teach the use of intrathecal administration of IL antagonists as in the present invention for suppression and inhibition of the action of IL in a human to treat neurological disease, trauma, injury or compression, or demyelinating neurologic disease, in which the IL antagonist provides the patient with a better opportunity to heal, slows disease progression, prevents neurological damage, or otherwise improves the patient's health.

Accordingly, it is an object of the present invention to provide IL antagonists as a new pharmacologic treatment of neurological disorders, trauma, injuries and compression affecting the nervous system of the human body; demyelinating neurologic disease; neurodegenerative diseases; retinal diseases; and muscular diseases; such that the use of these IL antagonists will result in the amelioration of these conditions.

Another object of the present invention is to provide IL antagonists for providing suppression and inhibition of the action of IL in a human to treat neurological injury, trauma or compression; demyelinating neurologic disease; neurodegenerative diseases; retinal diseases; and muscular diseases.

Another object of the present invention is to provide IL antagonists that reduce inflammation by inhibiting the action of IL in the human body for the immediate, short term (acute conditions) and long term (chronic conditions), such that this reduction in inflammation will produce clinical improvement in the patient and will give the patient a better opportunity to heal, slow disease progression, prevent neurological damage, prevent retinal and muscular damage, or otherwise improves the patient's health.

Another object of the present invention is to provide IL antagonists, using intrathecal administration as the preferred form of administration, that offer acute and chronic treatment regimens for neurological conditions caused by neurological trauma, compression, injury and/or disease, such conditions including acute spinal cord injury, herniated nucleus pulposus (herniated disc), spinal cord compression due to metastatic cancer, primary or metastatic brain tumors, chronic pain syndromes due to metastatic tumor, increased intracranial pressure, demyelinating diseases such as multiple sclerosis, inflammatory CNS diseases, such as subacute sclerosing panencephalitis, other related neurological disorders and diseases, retinal disorders, and muscular disorders.

SUMMARY OF THE INVENTION

The present invention provides a method for inhibiting the action of IL for treating neurological, retinal, and muscular disorders in a human by administering to the human therapeutically effective doses of IL antagonists for reducing the inflammation of neuronal, retinal, or muscular tissue of the human and/or preventing immune system damage to neuronal, retinal, or muscular tissue. The preferred forms of administration are intrathecal and intracerebroventricular administration into the cerebrospinal fluid (CSF).

DETAILED DESCRIPTION OF THE PREFERRED EMBODIMENTS

IL antagonist regimens to be used for neurological disorders are designed in two general ways: 1) acute regimens, designed to achieve rapid blood levels and rapid action, wherein IL blockade is desired for hours to days; and 2) chronic regimens, wherein IL blockade is desired for days, weeks, or months. Currently investigational IL-1 antagonists which are suitable for these regimens are IL1-R type II (interleukin 1 receptor type II) from Immunex Corporation and IL1-RA (interleukin 1 receptor antagonist) from Amgen Corporation.

Trauma, injury, compression and other neurological disorders can affect individual nerves, nerve roots, the spinal cord, or the brain. The disorders which are of most concern here are the following:

Alzheimer's Disease

Parkinson's Disease

Postherpetic Neuralgia

Pick's Disease

Huntington's Disease

Neurodegenerative Diseases

AIDS Dementia Complex

Inflammatory Diseases of the Brain, Spinal Cord, or Retina

Autoimmune Diseases of the Brain, Spinal Cord, or Retina

Multiple Sclerosis

Spinal Cord Injury

Spinal Cord Compression

Herniated Disc

Guillain-Barre Syndrome

Traumatic Brain Injury

Muscular Dystrophy

Polymyositis—Dermatomyositis

Intrathecal administration of IL antagonists is the preferred way to treat neurologic trauma, injury, compression and neurological disorders in comparison with steroids. Experimental evidence has shown that excessive levels of IL are released by injury to neuronal tissue. Accordingly, the use of IL antagonists will result in amelioration of these neurological conditions. Because of the profoundly powerful action of the new IL antagonists, they can prevent neurologic injury in a unique way, filling an urgent clinical need for more effective therapy. Also, these antagonists have an extremely safe side effect profile. Importantly, the IL antagonists lack the adverse effects of steroids as previously described. Lastly, steroids are only partially effective or completely ineffective. Intrathecal administration of IL antagonists is also the preferred way to treat retinal disorders.

Types of IL-1 Inhibitors

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Monoclonal antibodies with a high affinity for a specific cytokine will tend to reduce the biologic activity of that cytokine. Substances which reduce the biologic effect of a cytokine can be described in any of the following ways: as a cytokine blocker; as a cytokine inhibitor; or as a cytokine antagonist. In this patent we will use the terms blocker, inhibitor, and antagonist interchangeably with respect to interleukin.

Cytokine antagonists can take several forms. They may be monoclonal antibodies (defined above). They may take the form of a soluble receptor to that cytokine. Soluble receptors freely circulate in the body. When they encounter their target cytokine they bind to it, effectively inactivating the cytokine, since the cytokine is then no longer able to bind with its biologic target in the body. An even more potent antagonist consists of two soluble receptors fused together to a specific portion of an immunoglobulin molecule ($F_c$ fragment). This produces a dimer composed of two soluble receptors which have a high affinity for the target, and a prolonged half-life.

Interleukin-1 (IL-1) is a proinflammatory cytokine which has been implicated in the inflammatory response occurring in the brain, spinal cord, retina, muscle, and elsewhere in the body. There are two naturally occurring inhibitors of IL-1 in the body: IL-1 receptor antagonist (IL-1 RA) and IL-1 receptor type II (IL-1 R type II). Additional inhibitors of IL-1 for the purpose of this patent are soluble IL-1 receptors: fusion proteins consisting of two IL-1 receptors attached to the $F_c$ portion of a human IgG molecule (IL-1 R-FP); and monoclonal antibodies with a high affinity for IL-1.

A detailed discussion of each of the clinical conditions follows:

1) Acute Spinal Cord Injury:

About 10,000 cases occur per year in the U.S., with a current population of over 200,000 patients with residual neurologic damage, many of whom are paralyzed (quadriplegia or paraplegia). Current treatment for the acute injury is inadequate. In the early 1990's it was shown that early (within 8 hours of injury) treatment with high doses of steroids (methyl prednisolone) was beneficial for some of these patients. Surgical stabilization and spinal decompression is often necessary because of excessive swelling (edema) which can itself cause further severe injury to the cord due to further compression of the cord against its bony spinal canal. The etiology of most of these cases are motor vehicle accidents, with the remainder being sports injuries, falls, and other accidents. The window of opportunity for treatment is small, since massive swelling can occur within minutes.

The treatment regimen used here would be the acute regimen. This would involve the use of IL antagonists. A preferred regimen for acute spinal cord injury involves intrathecal administration. This acute regimen is a unique delivery method and is uniquely necessary for clinical neurologic conditions requiring rapid blockade of IL.

2) Demyelinating Disease, such as Multiple Sclerosis

Demyelinating neurological diseases, the most important being multiple sclerosis, are inadequately treated by currently available therapies, and continue to produce progressive, severe, neurologic impairment in a large population of patients in the United States and worldwide. There is experimental evidence which documents the role of IL in multiple sclerosis. There is a wide body of work which documents the role of both cellular and humoral immunity in multiple sclerosis. Using IL antagonists represents a novel approach to the treatment of these important disorders.

Several novel approaches are suggested. For acute demyelinating disease, it is paramount to use therapy which is rapidly effective to prevent permanent neurological damage. In this case, novel routes of administration of the IL antagonists may be used. These novel routes include intrathecal administration. These novel regimens are designed as such because of the mechanisms of action and low toxicity of these biopharmaceutical agents.

3) Neurodegenerative Diseases:

Alzheimer's Disease, Parkinson's Disease, Huntington's Disease, Pick's Disease, Creutzfeld-Jakob Disease, and AIDS Dementia Complex are all chronic, progressive, incurable disorders which lack satisfactory treatment. They all have important components of inflammation in which interleukins are implicated as contributing to neuronal damage. Chronic administration of the interleukin antagonists discussed here will help reduce the inflammatory response and the immune response affecting the brain tissue in these disorders. Amelioration of disease progression will occur, resulting in improvement in the patient's clinical condition. For all of these central nervous system conditions chronic administration of interleukin antagonists directly into the cerebrospinal fluid, either at the level of the spinal cord or into the cerebroventricular system, is the preferred method.

4) Herniated Nucleus Pulposus (Herniated Disc):

Low back pain affects 70% of the population during their lifetime, with 25% of this group having pain in the sciatic distribution. Current pharmacologic treatment is inadequate, consisting of analgesics and anti-inflammatory medications, such as nonsteroidal antiinflammatories (NSAIDS), such as ibuprofen (Motrin, etc.) and epidural steroid injections (generally regarded as having limited usefulness. Many of these patients eventually have surgery. Complications of lumbar disc herniation include permanent damage to the sciatic nerve, causing muscle weakness and atrophy in the lower extremity. Acute herniation with rapid onset of pain and sciatic nerve symptoms could be treated with the above acute regimen, with or without addition of the chronic regimen (described below), if symptoms continued. An alternative acute regimen for sciatica involves the subcutaneous bolus injection of an IL antagonist into the subcutaneous tissue directly overlying the area of sciatica involvement. This produces an enhanced therapeutic level of the mediation at the target site due to direct local absorption. Treatment could also be reserved for patients not responding to conventional therapy. The acute treatment regimen, as outlined above, could be used for patients in whom rapid control of symptoms was desired. Herniated cervical discs would be treated the same way as herniated lumbar discs with the need for careful evaluation by a neurologist, neurosurgeon, and/or orthopedic surgeon for signs of neurologic compromise kept in mind.

5) Spinal Cord Compression due to Metastatic Cancer:

Cord compression due to metastatic cancer is a catastrophic event leading to rapid paralysis if not quickly diagnosed and treated. It is most common with cancers of the breast, colon, lung and prostate, but can be a complication of metastatic disease from a wide variety of malignancies, including melanoma and multiple myeloma. Current treatment regimens include high dose steroids, emergency radiation treatment, and/or emergent surgical decompression. Paralysis can occur within hours, so treatment must be initiated within this time period to avoid permanent sequelae. The mechanism of action IL blockade here would be similar to that above. In addition, it is possible that IL blockade could be directly tumoricidal or tumoristatic with certain malignancies. Impending cord compression could be treated with the chronic regimen. However, as explained above, most patients would need to be emergently treated with the acute regimen, as outlined above.

6) Primary or Metastatic Brain Tumors:

Primary brain tumors can be either benign (most commonly meningioma) or malignant (usually gliomas). Metastatic brain tumors can be from any source, most commonly lung cancer, breast cancer, or other malignancies such as melanoma. Treatment for these tumors is primarily surgery or radiation, with generally poor response to chemotherapy. Many of these tumors cause surrounding edema which can cause further neurologic deterioration. IL blockade, either the acute or chronic treatment regimen, would be beneficial while these patients are awaiting surgery. Additionally, IL blockade, as discussed above, would have direct tumor inhibiting properties.

7) Chronic Pain Syndromes due to Metastatic Tumor:

Pain due to metastatic cancer is inadequately treated by currently used agents. It is probable that the mechanism of action of this pain is mediated in part by the overproduction of IL. IL blockade would be beneficial for selected tumors, particularly bone metastases where compression is involved. The chronic treatment regimens would be used. One general note of caution when treating malignancies is necessary: While IL blockade is likely to have an antitumor effect with certain malignancies, it is also possible that IL blockade could increase growth rates with certain malignancies.

8) Inflammatory CNS Diseases, such as Subacute Sclerosing Panencephalitis

Subacute sclerosing panencephalitis is a rare inflammatory disease of the brain, secondary to infection with a measles virus.

9) Huntington's Disease

Huntington's disease (Huntington's chorea) is a rare, progressive, fatal neurological disorder for which there is currently no effective treatment. It is often hereditary, and is characterized by a movement disorder (chorea), as well as progressive dementia.

10) Creutzfeld-Jakob Disease

Creuzfeld-Jakob disease, as well as New Variant Creuzfeld-Jakob disease, is one of the transmissible spongioform encephalopathies, along with Kuru and Scrapie and "Mad Cow Disease (Bovine spongioform encephalopathy)". These diseases are caused by infection with a new class of biologic agent called prions. These diseases are progressive, fatal, and can be contracted by ingesting tissue of an infected animal. There is no known treatment.

11) Parkinson's Disease

Parkinson's disease is a common neurologic disorder characterized by tremor, gait disorder, and dementia, for which there is no known cure.

12) Myasthenia Gravis

Myasthenia gravis is an autoimmune disorder of the neuromuscular junction, characterized by muscle weakness and easy fatiguability. There is no known cure. Corticosteroids are one of the mainstays of treatment.

13) Guillain-Barre Syndrome

Guillain-Barre syndrome is characterized by the rapid onset of weakness, usually in an ascending distribution, and often culminating in difficulty breathing. It often follows a preceding viral infection.

14) Bell's Palsy

Bell's palsy is characterized by the sudden onset of hemifacial paralysis, caused by acute mononeuropathy of the seventh cranial nerve, the facial nerve. It can follow viral infection, vaccination, or may be idiopathic. The mainstay of treatment is large doses of corticosteroids.

15) Diabetic Neuropathy

Diabetic neuropathy consists of a variety of clinical syndromes of neurologic damage occurring in patients with either juvenile onset or adult onset diabetes mellitus. Diabetic peripheral neuropathy causes sensory deficits, numbness, tingling, and painful paresthesias in the extremities. Diabetic autonomic neuropathy causes disorders of the autonomic nervous system, including diabetic gastropathy.

16) Amyotrophic Lateral Sclerosis

Amyotrophic lateral sclerosis is a progressive fatal, neurologic disease causing progressive weakness and cranial nerve palsies, causing difficulty with speech, eye movements, and such. There is no known cure.

17) Optic Neuritis

Optic neuritis is characterized by acute inflammation affecting the optic nerve, causing visual field defects. It is often part of Multiple Sclerosis, for which it may be the presenting symptom. Attacks can be intermittent and repeated.

18) Macular Degeneration

Macular degeneration is a leading cause of blindness, affecting predominantly the older population, for which there is no known cure.

19) Retinitis Pigmentosa

Retinitis pigmentosa is a hereditary retinal disease, resulting in blindness, for which there is no known cure.

20) Diabetic Retinopathy

Diabetic Retinopathy includes a spectrum of retinal disorders, including hemorrhage and exudates, which occur in patients with diabetes mellitus. Part of the retinopathy is due to a vascular damage caused by diabetes.

21) Muscular Dystrophy

Muscular dystrophy is a group of related diseases of muscle, many of which are hereditary, characterized by progressive muscular weakness. The cause and cure are unknown.

22) Polymyositis—Dermatomyositis

Polymyositis is an autoimmune inflammatory disease of muscle, characterized by progressive proximal muscle weakness and muscle wasting. Pathology shows an intense inflammatory infiltrate in the muscle. Treatment includes immunosuppressive drugs, corticosteroids, and respiratory support for more advanced cases. Dermatomyositis is polymyositis with a characteristic accompanying skin rash.

Combination Therapy

Treatment of neurologic, retinal, and muscular disorders may be accomplished by use of these Interleukin Antagonists singly; in combination with each other; or in combination with other medications.

For treatment of inflammatory and autoimmune disorders it may be useful to combine any of the agents described herein (interleukin antagonists) with other anti-inflammatory or immunosuppressive agents, or with other biologic agents. In particular, the combination of any of the agents described herein as IL Blockers with any of the following drugs offer advantages in terms of improved efficacy:

etanercept

TNF antagonists other than etanercept including, but not limited to D2 E7, infliximab, TNF alpha converting enzyme inhibitor (TACE inhibitor), and thalidomide methotrexate mitoxantrone leflunomide For example, certain patients with Alzheimer's Disease may show only a partial response to IL-1 antagonists. The addition of intrathecal TNF antagonists will further inhibit the inflammatory cascade, thereby further reducing neuronal damage, and causing greater clinical benefit. One preferred combination is intrathecal IL-1 RA with intrathecal etanercept for the treatment of Alzheimer's Disease.

Combination therapy will provide synergistic effects. Careful monitoring for adverse effects will be necessary because of the greater possibility of this occurring with drug combinations.

Dosages

General guidelines: substances administered by peripheral routes will require a higher dosage than those delivered by the intrathecal route. Peripheral routes of administration are defined herein as those which do not involve administration into the cerebrospinal fluid (CSF), for example, intranasal administration.

For example, IL-1 R-FP when administered subcutaneously will generally be effective at a dosage level of between 10 mg and 250 mg (mean dose of 50 mg); when given intrathecally doses of between 0.5 mg and 25 mg (mean dose of 10 mg) will generally be used.

Monoclonal antibodies will generally be used at somewhat higher dosages, usually 0.5–25 mg/kg when administered peripherally, and 0.1–1.0 mg/kg when given intrathecally.

IL-1 RA and IL-1 R type II dosages will be similar and will approximate 0.02 to 3.0 mg/kg when given daily by subcutaneous bolus injection, and 0.01 to 0.5 mg/kg when administered intrathecally.

Routes of Administration

For the muscular disorders listed above, the peripheral routes of administration may be employed. These include subcutaneous, intravenous, intramuscular, intranasal, oral, transepidermal, parenteral, mucosal, intrarectal, or by inhalation.

For the retinal disorders listed above, the peripheral routes of administration may be employed, or CSF administration may be employed.

For the neurological disorders listed above, the peripheral routes of administration may be employed, but CSF administration is the preferred route.

Administering the IL Blocker into the cerebrospinal fluid is performed by implanting in the scalp of the patient a subcutaneous reservoir for receiving the IL Blocker. The reservoir has an attached catheter to communicate with the cerebroventricular system of the patient. The reservoir is accessed by needle injection from the outside through the scalp, thereby allowing the introduction of the IL Blocker directly into the reservoir and the catheter in order to communicate and supply the IL Blocker into the cerebroventricular system.

Alternatively, the IL Blocker may be administered into the cerebrospinal fluid by implanting in the abdomen of the patient a subcutaneous reservoir for receiving the IL Blocker. The reservoir has an attached catheter to communicate with the intrathecal space of the patient, and the catheter is placed into the intrathecal space. The reservoir is accessed by needle injection from the outside through the skin, thereby allowing the introduction of the IL Blocker directly into the reservoir and the catheter in order to communicate and supply the IL Blocker into the cerebrospinal fluid.

ADVANTAGES OF THE PRESENT INVENTION

Accordingly, an advantage of the present invention is that it provides for IL antagonists as a new pharmacologic treatment of neurological disorders, trauma, injuries and compression affecting the nervous system of the human body; demyelinating neurologic disease; neurodegenerative diseases; retinal diseases; and muscular diseases; such that the use of these IL antagonists will result in the amelioration of these conditions.

Another advantage of the present invention is that it provides for IL antagonists for providing suppression and inhibition of the action of IL in a human to treat neurological injury, trauma or compression; demyelinating neurologic disease; neurodegenerative diseases; retinal diseases; and muscular diseases.

Another advantage of the present invention is that it provides for IL antagonists that reduce inflammation by inhibiting the action of IL in the human body for the immediate, short term (acute conditions) and long term (chronic conditions), such that this reduction in inflammation will produce clinical improvement in the patient and will give the patient a better opportunity to heal, slow disease progression, prevent neurological damage, prevent retinal and muscular damage, or otherwise improves the patient's health.

Another advantage of the present invention is that it provides for IL antagonists, using intrathecal administration as the preferred form of administration, that offer acute and chronic treatment regimens for neurological conditions caused by neurological trauma, compression, injury and or disease, such conditions including acute spinal cord injury, herniated nucleus pulposus (herniated disc), spinal cord compression due to metastatic cancer, primary or metastatic brain tumors, chronic pain syndromes due to metastatic tumor, increased intracranial pressure, demyelinating diseases such as multiple sclerosis, inflammatory CNS diseases, such as subacute sclerosing panencephalitis, other related neurological disorders and diseases, retinal disorders, and muscular disorders.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method for inhibiting the action of interleukin (IL) for treating neurological conditions in a human by administering an IL Blocker for reducing the inflammation of neuronal tissue or the neuromuscular junction of said human, or for modulating the immune response affecting neuronal tissue or the neuromuscular junction of said human, comprising the step of:

a) administering a therapeutically effective dosage level to said human of said IL Blocker for reducing the inflammation of neuronal tissue or the neuromuscular junction of said human, or for modulating the immune response affecting neuronal tissue or the neuromuscular junction of said human; and b) administering said IL Blocker into the cerebrospinal fluid (CSF) of said human.

2. A method for inhibiting the action of IL in accordance with claim 1, wherein said IL Blocker is selected from the group consisting of IL-1 RA, IL-1R type II, monoclonal antibodies to IL-1, soluble receptors to IL-1, and soluble receptors to IL-1 fused to an $F_c$ immunoglobulin fragment.

3. A method for inhibiting the action of IL in accordance with claim 2, wherein the step of administering said IL Blocker is performed through intrathecal administration for treating Alzheimer's disease.

4. A method for inhibiting the action of IL in accordance with claim 2, wherein the step of administering said IL Blocker is performed through intracerebroventricular administration for treating Alzheimer's disease.

5. A method for inhibiting the action of IL in accordance with claim 2, wherein the step of administering said IL-1 RA is performed through intrathecal administration or intracerebroventricular administration for treating Alzheimer's disease.

6. A method for inhibiting the action of IL in accordance with claim 2, wherein the step of administering said IL-1 R type II is performed through intrathecal administration or intracerebroventricular administration for treating Alzheimer's disease.

7. A method for inhibiting the action of IL in accordance with claim 2, wherein the step of administering said IL Blocker is performed through intrathecal administration.

8. A method for inhibiting the action of IL in accordance with claim 2, wherein the step of administering said IL Blocker is performed through intracerebroventricular administration.

9. A method for inhibiting the action of IL in accordance with claim 2, wherein the step of administering said IL-1 RA is performed through intrathecal administration or through intracerebroventricular administration.

10. A method for inhibiting the action of IL in accordance with claim 2, wherein the step of administering said IL-1 R type II is performed through intrathecal administration or through intracerebroventricular administration.

11. A method for inhibiting the action of IL in accordance with claim 1, wherein the step of administering said dosage level is for treating neurodegenerative diseases including Alzheimer's disease, Parkinson's disease, Huntington's disease, Pick's disease, and Creutzfeld-Jakob disease.

12. A method for inhibiting the action of IL in accordance with claim 1, wherein the step of administering said dosage level is for treating Alzheimer's disease.

13. A method for inhibiting the action of IL in accordance with claim 1, wherein the step of administering said dosage level is for treating AIDS Dementia Complex.

14. A method for inhibiting the action of IL in accordance with claim 1, wherein the step of administering said dosage level is for treating myasthenia gravis.

15. A method for inhibiting the action of IL in accordance with claim 1, wherein the step of administering said dosage level is for treating Guillain-Barre syndrome.

16. A method for inhibiting the action of IL in accordance with claim 1, wherein the step of administering said dosage level is for treating Bell's palsy.

17. A method for inhibiting the action of IL in accordance with claim 1, wherein the step of administering said dosage level is for treating neurological traumas and injuries, and for treating neurological diseases and disorders.

18. A method for inhibiting the action of IL in accordance with claim 1, wherein the step of administering said dosage level is for treating acute spinal cord injury or brain injury.

19. A method for inhibiting the action of IL in accordance with claim 1, wherein the step of administering said dosage level is for treating primary or metastatic brain tumors.

20. A method for inhibiting the action of IL in accordance with claim 1, wherein the step of administering said dosage level is for treating chronic pain syndrome due to metastatic tumor.

21. A method for inhibiting the action of IL in accordance with claim 1, wherein the step of administering said dosage level is for treating herniated disc.

22. A method for inhibiting the action of IL in accordance with claim 1, wherein the step of administering said dosage level is for treating central nervous system lesions.

23. A method for inhibiting the action of IL in accordance with claim 1, wherein the step of administering said dosage level is for treating autoimmune neurological diseases.

24. A method for inhibiting the action of IL in accordance with claim 1, wherein the step of administering said dosage level is for treating multiple sclerosis.

25. A method for inhibiting the action of IL in accordance with claim 1, wherein the step of administering said dosage level is for treating inflammatory CNS diseases including subacute sclerosing panencephalitis.

26. A method for inhibiting the action of IL in accordance with claim 1, wherein the step of administering said dosage level is for treating amyotrophic lateral sclerosis.

27. A method for inhibiting the action of IL in accordance with claim 1, wherein the step of administering said dosage level is for treating inflammatory diseases of the brain, spinal cord or retina.

28. A method for inhibiting the action of IL in accordance with claim 1, wherein the step of administering said dosage level is for treating autoimmune diseases of the brain, spinal cord or retina.

29. A method for inhibiting the action of IL in accordance with claim 1, wherein the step of administering said IL Blocker into the cerebrospinal fluid is performed by implanting in the scalp of said human a subcutaneous reservoir for receiving said IL Blocker, said reservoir having an attached catheter to communicate with the cerebroventricular system of said human, and accessing said reservoir by needle injection from the outside through the scalp of said human, thereby allowing the introduction of said IL Blocker directly into said reservoir and said catheter to communicate and supply said IL Blocker into the cerebroventricular system.

30. A method for inhibiting the action of IL-1 in accordance with claim 1, wherein the step of administering said IL Blocker into the cerebrospinal fluid is performed by implanting in the abdomen of said human a subcutaneous reservoir for receiving said IL Blocker, said reservoir having an attached catheter to communicate with the intrathecal space of said human, placing said catheter into the intrathecal space of said human, and accessing said reservoir by needle injection from the outside through the skin of said human, thereby allowing the introduction of said IL Blocker directly into said reservoir and said catheter to communicate and supply said IL Blocker into the cerebrospinal fluid.

* * * * *

UNITED STATES PATENT AND TRADEMARK OFFICE
CERTIFICATE OF CORRECTION

PATENT NO. : 6,471,961 B1
DATED : October 29, 2002
INVENTOR(S) : Edward L. Tobinick It is certified that error appears in the above-identified patent and that said Letters Patent is hereby corrected as shown below:

<u>Title page,</u>
Insert Item:
-- Related U.S. Application Data
[63]   This application is a continuation-in-part of Application Serial No. 09/476,643, filed on December 31, 1999, now U.S. Patent No. 6,177,077, which is a continuation-in-part of Application Serial No. 09/275,070, filed on March 23, 1999, now U.S. Patent No. 6,015,557, which is a continuation-in-part of Application Serial No. 09/256,388, filed on February 24, 1999, now abandoned. --.

Signed and Sealed this

Twenty-third Day of May, 2006

JON W. DUDAS
*Director of the United States Patent and Trademark Office*